(12) United States Patent
Neal et al.

(10) Patent No.: US 7,192,470 B2
(45) Date of Patent: *Mar. 20, 2007

(54) PRESERVATIVE COMPOSITIONS FOR MATERIALS AND METHOD OF PRESERVING SAME

(75) Inventors: Edwin Neal, Santa Rosa Beach, FL (US); Michael M. Thompson, Maryland Heights, MO (US)

(73) Assignee: Woodholdings Environmental, Inc., Marco Island, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/039,515

(22) Filed: Jan. 19, 2005

(65) Prior Publication Data

US 2006/0088605 A1    Apr. 27, 2006

Related U.S. Application Data

(63) Continuation-in-part of application No. 10/297,398, filed on May 27, 2003.

(51) Int. Cl.
*A01N 55/10*     (2006.01)
*A01N 59/14*     (2006.01)
*B05D 7/00*      (2006.01)
*B05D 7/06*      (2006.01)
*B05D 1/18*      (2006.01)

(52) U.S. Cl. .................. 106/18.35; 106/3; 106/15.05; 106/18.13; 106/18.3; 424/657; 427/297; 427/384; 427/387; 427/397; 514/63

(58) Field of Classification Search ............ 106/15.05, 106/18.3, 3, 18.35, 18.13; 424/457, 458, 424/459, 460, 657; 514/63; 427/297, 384, 427/387, 397
See application file for complete search history.

(56) References Cited

U.S. PATENT DOCUMENTS

| | | | |
|---|---|---|---|
| 2,306,222 A | 12/1942 | Patnode | |
| 2,412,470 A | 12/1946 | Norton | |
| 3,637,570 A | 1/1972 | Stout | |
| 3,682,675 A | 8/1972 | Myers | |
| 3,986,999 A | 10/1976 | Sattlegger et al. | |
| 4,002,800 A | 1/1977 | Nestler et al. | |
| 4,013,474 A | 3/1977 | Teitell et al. | |
| 4,386,134 A | 5/1983 | Pühringer | |
| 4,423,112 A | 12/1983 | Luthringshauser et al. | |
| 4,491,669 A * | 1/1985 | Arkles et al. ............... | 556/410 |
| 4,534,815 A | 8/1985 | Hamada et al. | |
| 4,544,413 A | 10/1985 | Boots et al. | |
| 4,859,359 A | 8/1989 | DeMatteo et al. | |
| 5,073,195 A | 12/1991 | Cuthbert et al. | |
| 5,120,581 A | 6/1992 | Brunken | |
| 5,204,186 A | 4/1993 | Brunken et al. | |
| 5,413,808 A | 5/1995 | Wyner | |
| 5,652,026 A | 7/1997 | Saka et al. | |
| 5,871,817 A | 2/1999 | Nasheri | |
| 5,990,043 A | 11/1999 | Kugler et al. | |
| 2002/0110644 A1 | 8/2002 | Kelsoe | |
| 2003/0059545 A1 | 3/2003 | Kelsoe | |
| 2003/0087035 A1 | 5/2003 | Kelsoe | |

FOREIGN PATENT DOCUMENTS

| | | |
|---|---|---|
| CA | 2236893 | 11/1998 |
| DE | 39 00 303 A1 | 7/1990 |
| EP | 0 339 957 A2 | 11/1989 |
| EP | 0 747 184 A2 | 12/1996 |
| JP | 56-38366 | 4/1981 |
| JP | 57036168 | 2/1982 |
| JP | 1-305006 | 12/1989 |
| JP | 2-6488 | 1/1990 |
| JP | 5-43838 | 2/1993 |
| JP | 8-318509 | 12/1996 |
| JP | 09087115 | 3/1997 |
| JP | 9-300312 | 11/1997 |
| JP | 10251599 | 9/1998 |
| JP | 11-92694 | 4/1999 |
| JP | 2000-80354 | 3/2000 |
| PL | 148704 | 3/1990 |
| SE | 502117 | 8/1995 |
| WO | WO 97/02119 | 1/1997 |
| WO | WO 01/93685 A1 | 12/2001 |
| WO | WO 01/97985 A1 | 12/2001 |

OTHER PUBLICATIONS

Derwent Abstract No. 1989-107-092, abstract of German Patent Specification No. 262019A (Nov. 16, 1988).

* cited by examiner

*Primary Examiner*—Anthony J. Green
(74) *Attorney, Agent, or Firm*—Bliss McGlynn, P.C.

(57) ABSTRACT

Preservative composition for various materials and method of preserving the same is disclosed. The preservative composition includes at least one silane-containing material and at least one hydrocarbon solvent containing molecules of at least five carbon atoms.

22 Claims, No Drawings

PRESERVATIVE COMPOSITIONS FOR MATERIALS AND METHOD OF PRESERVING SAME

CROSS-REFERENCE TO RELATED APPLICATIONS

This application is a continuation-in-part of U.S. Ser. No. 10/297,398, entitled "Preservative Compositions for Wood Products," filed May 27, 2003, which claims the benefit of Section 371 of PCT Application No. PCT/US01/18280, filed Jun. 6, 2001, which claims the benefit of U.S. Provisional Application No. 60/209,743, filed Jun. 6, 2000.

BACKGROUND OF THE INVENTION

1. Field of the Invention

The present invention relates generally to preservative compositions and, more particularly, to preservative compositions for materials and to a method for preserving the same.

2. Description of the Related Art

Certain materials are susceptible to damage caused by the elements, especially water and insects (e.g., termites, certain types of ants, and other boring insects). For instance, exposure to water typically causes many materials, such as various wood products, insulation, newsprint, drywall, and masonry bricks, to crack, warp, check, as well as become discolored and mildewed. Also, water and/or insect damage often causes these materials to rot and decay. Typically, water and/or insect damage leads to the eventual replacement of the damaged section of the material at great expense, effort, and inconvenience.

Preservative manufacturers have marketed various treatment products that supposedly prevent, or reduce the likelihood of water and/or insect damage to the material to which the treatment products are applied. However, these treatment products have not been completely satisfactory, especially with regard to effectiveness, cost concerns, ease of application, duration of treatment time, and duration of protection afforded.

Therefore, it is desirable to provide a preservative composition for various materials. It is also desirable to provide a preservative composition that preserves various materials effectively against water intrusion and damage. Further, it is desirable to provide a preservative composition that preserves materials effectively against insect intrusion and damage. Still further it is desirable to provide a preservative composition that is relatively inexpensive. It is also desirable to provide a preservative composition that is relatively easy to apply. Furthermore, it is desirable to provide a preservative composition that has a relatively short treatment time. Also, it is desirable to provide a preservative composition that provides a relatively long period of protection. Therefore, there is a need in the art to provide a preservative composition and method that meets these desires.

SUMMARY OF THE INVENTION

It is, therefore, one object of the present invention to provide new preservative compositions for various materials and methods for preserving the same.

It is another object of the present invention to provide new preservative compositions for various materials that protect the materials against water intrusion and/or insect damage.

To achieve the foregoing objects, the present invention is a preservative composition for materials including at least one silane-containing material and at least one hydrocarbon solvent containing molecules of at least five carbon atoms.

In addition, the present invention is a method for preserving a material including the steps of providing a composition having at least one silane-containing material and at least one hydrocarbon solvent containing molecules of at least five carbon atoms, and contacting the material with the composition.

One advantage of the present invention is that a new preservative composition for various materials is provided. Another advantage of the present invention is that the preservative composition preserves various materials effectively against water intrusion and damage. Yet another advantage of the present invention is that the preservative composition preserves materials effectively against insect intrusion and damage. Still another advantage of the present invention is that the preservative composition is relatively inexpensive. A further advantage of the present invention is that the preservative composition is relatively easy to apply. Yet a further advantage of the present invention is that the preservative composition has a relatively short treatment time. Still a further advantage of the present invention is that the preservative composition provides a relatively long period of protection.

Other objects, features and advantages of the present invention will be readily appreciated, as the same becomes better understood, after reading the subsequent description taken in conjunction with the accompanying drawings.

DESCRIPTION OF THE PREFERRED EMBODIMENT(S)

The present invention includes compositions, and methods of use therefor, for preserving, protecting, and treating subject materials so as to impart protection against various sources of damage, including, but not limited to water and insects. The terms "preserving," "protecting," and "treating," as those terms are used interchangeably herein, are meant to include any methods of, and compositions for, protecting subject materials from damage caused by any source, including, but not limited to water and insects. The term "subject material" as used herein is meant to include any object that can be preserved, protected, and treated with the compositions of the present invention, including but not limited to wood products (i.e., products containing any amount of wood), insulation, paper used to coat insulation, drywall, newsprint, and masonry brick.

In accordance with one embodiment of the present invention, the preservative composition includes at least one silane-containing material and at least one solvent.

The preservative composition contains at least one silane-containing material. Silanes are generally defined in a class of silicon-based materials, analogous to alkanes, that is, straight-chain, saturated paraffin hydrocarbons having the general formula $Si_NH_{2N+2}$, wherein N is an integer equal to 1 or higher. The silane-containing material is preferably in the form of trichloromethylsilane (chemical formula: $CH_3Cl_3Si$), although other forms of silane-containing materials are acceptable. Examples of other silane-containing materials useful in practicing the present invention include, without limitation:

(Chloromethyl) Trichlorosilane;
[3-(Heptafluoroisoproxy)Propyl]Trichlorosilane;
1,6-Bis(Trichlorosilyl)Hexane;
3-Bromopropyltrichlorosilane;

Allylbromodimethylsilane;
Allyltrichlorosilane;
Bromomethylchlorodimethylsilane;
Bromothimethylsilane;
Chloro(Chloromethyl)Dimethylsilane; Chlorodiisopropyloctylsilane;
Chlorodiisopropylsilane;
Chlorodimethylethylsilane;
Chlorodimethylphenylsilane;
Chlorodimethylsilane;
Chlorodiphenylmethylsilane;
Chlorotriethylsilane;
Chlorotrimethylsilane;
Dichlorodimethylsilane;
Dichloromethylsilane;
Dichloromethylvinylsilane;
Diphenyldichlorosilane;
Di-t-Butylchlorosilane;
Ethyltrichlorosilane;
Iodotrimethylsilane;
Pentyltrichlorosilane;
Phenyltrichlorosilane;
Trichloro(3,3,3-Trifluoropropyl)Silane;
Trichloro(Dichloromethyl)Silane; and
Trichlorovinylsilane.

The preservative composition contains at least one solvent. The solvent is in the form of a hydrocarbon. For example, hydrocarbons which are liquid at room temperature are acceptable. Examples of these hydrocarbons are hydrocarbons having molecules of at least five carbon atoms that include, without limitation, pentane, hexane, and heptane. It should be appreciated that, although a hydrocarbon solvent is used, other organic solvents such as tetrahydrofuran (THF) may be used.

In accordance with another embodiment of the present invention, the preservative composition includes at least pesticide-containing material, at least one silane-containing material, and at least one solvent.

The pesticide-containing material is preferably in the form of boric anhydride (chemical formula: $B_2O_3$), although other forms of boron-containing materials are acceptable. By way of a non-limiting example, borax (chemical formula: $Na_2B_4O_7 \cdot H_2O$), and disodium octaborate tetrahydrate (chemical formula: $Na_2B_8O_{13} \cdot H_2O$) may be used as well. Effective fungal and fire resistance can be obtained with a boron loading of 0.1 weight percent, based on the total weight of the subject material. However, in order to prevent wood-boring insect infestation (e.g., by ants and termites), a loading of 1–2 weight percent of boron is generally required. For more problematic insects, such as the Formosan termite, a loading of 7 weight percent of boron is generally required. Therefore, the present invention provides a product, and a method of using the same, to introduce pesticide-containing material such as boron into the subject material at levels of at least about 0.1 to at least about 7 weight percent and seal it to prevent environmental factors (e.g., rain) from leaching it from the interior of the subject material. It should be appreciated that other organic pesticide-containing materials other than boron may be used.

The preservative composition may include other additives. Other additives such as paint or stain may be used. The additives are carried with the hydrocarbon solvent and silane-containing material and penetrate the material being treated. For example, colorant may be an additive to the preservative composition to treat and color wood product. It should be appreciated that other types of organic additives may be used to treat the materials.

METHOD OF PRESERVING MATERIALS & MATERIALS TO BE PRESERVED

In order to preserve various materials using the preservative composition of the present invention, the preservative composition is prepared. Then, the preservative composition is applied to the material to be preserved. For instance, the preservative composition is topically applied to the material to be preserved. The preservative composition of the present invention can be applied to preserve several types of various materials, including but not limited to the following: 1) wood materials, such as newsprint and other paper products; 2) insulation materials, such as paper-coated polyurethane-filled insulation; 3) drywall materials, such as sheet rock; 4) masonry materials, such as masonry brick; and 5) fibrous material such as cotton. It should be appreciated that, for specific wood products such as telephone poles and railroad ties, a lower hydrocarbon solvent may be used such as diesel fuel may be used in the preservative composition.

The preparation of an illustrative preservative composition, in accordance with the general teachings of the present invention, is presented in Example I, below:

EXAMPLE I

Approximately 50 ml of THF was added to a 250 ml Erlenmeyer flask. Approximately 1.0 µm of boric anhydride ($B_2O_3$) was added to the flask and stirred. The mixture was cloudy at first, but gradually cleared upon sitting for 5 minutes. A small amount of $B_2O_3$ remained on the bottom of the flask. Approximately 10 to 15 ml of trichloromethylsilane was then slowly added to the solution. No visual evidence of an exothermic reaction was observed. The solution remained clear.

In order to determine the effectiveness of the illustrative preservative composition prepared in Example I, a comparison test was performed between a treated portion and an untreated portion of a piece of plywood board. The results of the comparison test are presented in Example II, below:

EXAMPLE II

An eyedropper was used to deposit several drops of the preservative composition prepared in Example I to a piece of plywood board. No evidence of an exothermic reaction or the evolution of foul smelling HCl gas was observed with the addition of the prepared solution to the wood sample. The composition diffused laterally across the surface of the board in addition to vertically through the board. Water was poured onto the treated area and it effectively repelled the water. The water was immediately absorbed in the untreated portion. Several drops were also deposited on the edge of the board to determine the effect of the solvent (i.e., THF) on the glue. A screwdriver and a spatula were used to try to separate the layers. This effort was unsuccessful.

In order to further determine the effectiveness of the illustrative preservative composition prepared in Example I, a comparison test was performed between a treated portion and an untreated portion of a piece of hardwood. The results of the comparison test are presented in Example III, below:

EXAMPLE III

Several drops of the preservative composition prepared in Example I were applied to a solid piece of hardwood. The sample was allowed to sit for several minutes prior to exposing it to water. Upon drying, no white residue was observed on the surface of the sample. Water was repelled off both sides of the sample even though just one side was treated.

The preparation of another illustrative preservative composition, in accordance with the general teachings of the present invention, is presented in Example IV, below:

EXAMPLE IV 20 ml of THF was added to a 100 ml beaker. Approximately 1 gm of $B_2O_3$ and 1 ml of trichloromethylsilane was added to the THF solvent. The total volume was approximately 22 ml.

In order to determine the effectiveness of the illustrative preservative composition prepared in Example IV, a comparison test was performed between a treated portion and an untreated portion of a piece of plywood board. The results of the comparison test are presented in Example V, below:

EXAMPLE V

A piece of plywood, 5/8 inches×5/8 inches×3½ inches was placed into a beaker and partially submerged into the preservative composition prepared in Example IV. The beaker was covered for approximately 5 minutes. After 5 minutes, the piece of plywood was removed and allowed to air dry. The volume of the preservative composition remaining in the beaker had been reduced by 2–3 ml, or about 10%. There was no visible white deposit on the surface of the plywood. Surface samples were removed from both the treated and untreated portions of the plywood in order to evaluate them under a microscope. There was an observable difference between the samples. The treated plywood appeared as though it had been coated in glass or white cotton coating. There was a difference in the appearance of the heartwood and the sapwood. The cells of the untreated plywood appeared empty, while those of the treated wood appeared to be coated with glass. When drops of methanol were added to the plywood samples, the treated sample beaded up and looked like a jelly on the surface of the sample. Whereas, the run off water was readily absorbed on the untreated plywood. A piece (½ inch×½ inch×¾ inches) of this plywood was placed in a 100 ml beaker containing 10 ml of water and covered with a watch glass. The sample was allowed to sit undisturbed for 24 hours and then the plywood was removed from the water. The FTIR of the water from the leaching experiment showed a slight peak @ 800 cm−1. The peak was not strongly defined as in the case of the silane reference peaks. The treated plywood showed no sign of silanes on the surface after being soaked in water for 24 hours. It did, however, readily repel water on all sides. The cut surface also repelled water even though it was never in direct contact with the preservative composition. It was ½ inch to ¾ inches away from the preservative composition.

There were several benefits that were observed for using a solvent, such as THF, over just a neat application of methyltrichlorosilane, including: (1) costs were reduced by dilution (e.g., with THF) of the neat methyltrichlorosilane solution; (2) no evidence of an exothermic reaction was observed; (3) no white residue was left on the surface of the treated subject material; (4) boron and silane readily penetrated into and diffused through the subject material and were delivered in one step; (5) little or no drying time was necessary prior to use; (6) cycle treatment time was drastically reduced over the CCA process; (7) no delamination or degradation of plywood was observed; (8) the treated subject material was rendered waterproof; (9) the treated subject material was rendered insect resistant (by virtue of the boron present); (10) the treated subject material was rendered fire resistant (by virtue of the boron present); and (11) the treated subject material resisted leaching.

In order to determine the boron penetration and retention characteristics of the preservative composition of the present invention, an experiment was carried out as described in Example VI, below:

EXAMPLE VI

In a 2 liter Erlemneyer flask, 800 milliliters of THF was added. A magnetic stirring bar began stirring at a low rate. To this stirred solution, 6.895 grams (0.7 percent by weight of solvent) of $B_2O_3$ was slowly added. The mixture was allowed to stir for 20 to 30 minutes. The solution was clear, although some undissolved $B_2O_3$ did remain on the bottom of the flask. To this stirred solution, 200 milliliters of methyltrichlorosilane was transferred via nitrogen pressurized canula, over a 10 minute period. The system was well behaved and no evidence of an exothermic reaction was observed. This resulted in an approximate 20 volume percent methyltrichlorosilane solution. The solution was stirred for 10 minutes and then stirring was ceased. A small amount of undissolved $B_2O_3$ remained on the bottom of the flask. A 500 milliliter aliquot was decanted into each of two 1 liter beakers and covered with a large watch glass. A first set of wood blocks had the dimensions of 1 inch×2 inches×5/8 inches. A second set of wood blocks were ¾ inch cubes. The wood blocks from each sample were placed individually into their respective solutions. A smaller watch glass was placed inside the beaker such that the weight of the watch glass kept the wood block samples completely submerged. The samples were allowed to stand in the solution for 1 hour. Some bubbling took place throughout the entire process. After the 1 hour treatment, the wood blocks were removed from the solution and allowed to air dry overnight. The pieces of wood appeared to "smoke" while drying. The smoke was believed to be hydrochloric acid. It is probably produced from the hydrolysis of the unreacted methyltrichlorosilane present on the surface of the wood. The solution appeared turbid and slightly discolored following the treatment.

It was observed that one hour is probably too long to expose wood to the preservative composition as described above. The treated wood has a tendency to smoke (i.e., evolve HCl) due to excess silane on the surface of the wood. A 5 to 10 minute exposure to the preservative composition as described above is probably more than sufficient to achieve the aforementioned benefits.

Additionally, the appearance of the wood treated with the preservative composition as described above for 1 hour is gray or ashen in appearance. This is probably due to the boron. This feature is not present in the material treated for 5 to 10 minutes with the preservative composition as described above.

In accordance with an alternative embodiment of the present invention, the boron-containing material is preferably impregnated into the subject material prior to, and separately from, impregnation by the silane-containing material.

It was observed that the most effective method for introducing boron into wood products, at a concentration of 1 weight percent or greater (based on the total weight of the treated wood product), is with the use of water as the solvent, as opposed to hydrocarbons such as THF, and preferably under the influence of a pressurized treatment vessel.

Although THF was used initially as a solvent for the boron-containing material because it is commonly used in boron chemistry, the problem is that boron is marginally soluble in THF and repeated treatment cycles must be used in order to reach 1 weight percent boron loading in the untreated wood product. Accordingly, because of the differences in the types of solvents needed, it is preferred that the boron-containing material be introduced into the wood products prior to, and separately from, the introduction of the silane-containing material into the wood product.

Following a four hour treatment period with the boron-containing material/water solution, this should result in a final boron concentration of 2 weight percent. It should be noted that higher boron loading concentrations could be achieved by varying (e.g., increasing) the boron concentration in the boron-containing treatment solution and/or by varying (e.g., increasing) the treatment period. It was then determined whether the wet, treated wood product (i.e., boron-impregnated) could be subsequently treated with the silane-containing material (e.g., methyltrichlorosilane solution) to yield acceptable results.

In accordance with an alternative embodiment of the present invention, it was observed that the performance and cost of the pentane solvent is superior to that of THF for the purpose of applying the methyltrichlorosilane to wet, boron-impregnated wood products.

By way of a non-limiting example, a preferred concentration of methyltrichlorosilane in pentane, wherein the methyltrichlorosilane is present at 1 to 3 volume percent, should be used in the treatment of boron-impregnated wood products. For example, thick wood products such as railroad ties may require higher levels of the methyltrichlorosilane to be present, whereas thinner wood products, such as planking for fences and decks and dimensional lumber, may require lower levels of the methyltrichlorosilane to be present. However, at least one exposed (untreated or unpainted) surface will generally be necessary in order to introduce boron-containing materials into pre-existing wooden structures.

In order to determine the silane penetration characteristics of the alternative methodology on treated (i.e. boron-impregnated) wood products, an experiment was carried out as described in Example VII, below:

EXAMPLE VII

Initially, a 1 volume percent solution of methyltrichlorosilane/pentane was prepared and applied to a piece of wood saturated with water. A second solution, with a 3 volume percent concentration of methyltrichlorosilane/pentane, was also prepared and tested. Two separate pieces of water-saturated wood were sprayed immediately following the removal of the wood from a boron-containing treatment vessel. The wood pieces had been previously treated with the pressurized aqueous solution of boron-containing material for 2 hours. The wood did not appear to repel or bead water immediately following the treatment. However, as the wood dried, it displayed evidence of complete water repulsion. Following a 24 hour drying time, the exterior of the 1 volume percent solution treatment indicated partial waterproofing capability. No observable coating was evident on the surface of the wood. Following a 24 hour drying time, the exterior of the 3 volume percent solution treatment was completely waterproof. Upon breaking the wood in half and exposing an interior surface, the penetration of the silane was evident at the thickness of a human hair. Better results were obtained when additional wood pieces were treated with the 3 volume percent concentration of methyltrichlorosilane/pentane solution in time intervals of 30 minutes, 2.5 hours, 1 week, 2 weeks, and 4 weeks, after removal of the sample wood pieces from the boron-containing treatment vessel. This may indicate that it may not be possible to treat totally wet wood, and it may be necessary to partially dry the wood prior to the application of the methyltrichlorosilane/pentane solution.

The performance of the solvent pentane appeared to be superior to THF when applying the methyltrichlorosilane to the treated wood. The reactivity of the methyltrichlorosilane was reduced and no appreciable amounts of hydrochloric acid (HCl) gas was observed following treatment. This may be due, in part, to the fact that the silane was present in concentrations of 3 volume percent or less.

Furthermore, when sprayed topically on the surface of a latex painted piece of wood, the methyltrichlorosilane/pentane solution penetrates the paint layer and effectively seals the wood layer below the paint surface. When sprayed topically on the surface of an oil-based painted piece of wood, the methyltrichlorosilane/pentane solution penetrates the paint layer and effectively seals the wood layer below the paint surface.

In order to determine the silane penetration characteristics of the alternative methodology on a subject material having painted surfaces, an experiment was carried out as described in Example VIII, below:

EXAMPLE VIII

A 3 volume percent solution of methyltrichlorosilane/pentane was prepared and introduced to a 1-gallon plastic pump sprayer. This solution was then sprayed topically on the surface of latex and oil-based painted blocks of wood. A single pass spraying resulted in the incorporation of the silane beneath the surface of the paint. Extensive spraying appeared to reduce the thickness of the latex paint. The penetration was observed approximately 1 inch deep into the wood matrix. No amount of spraying appeared to diminish the thickness or adhesion of the oil-based paint on the surface of the wood.

The waterproofing penetration of the 1 volume percent solution of methyltrichlorosilane in pentane is preferably 0.75 inches, and the waterproofing penetration of the 3 volume percent solution of methyltrichlorosilane in pentane is preferably 1.5 inches.

In order to determine the silane penetration characteristics of the alternative methodology on untreated subject materials, an experiment was carried out as described in Example IX, below:

EXAMPLE IX

Both of the 1 and 3 volume percent methyltrichlorosilane/pentane solutions were applied to fresh red oak blocks in order to determine the penetration ability of the solutions. A quick single spray pass was applied to each block of wood. The waterproofing penetration of the 1 volume percent solution of methyltrichlorosilane in pentane was 0.75 inches. The waterproofing penetration of the 3 volume percent solution of methyltrichlorosilane in pentane was 1.5 inches. The level of penetration was determined by splitting cross-sectional pieces of wood off of the block and then introducing the wood sample to a small stream of water. The boundary of the treated and untreated wood could then be determined.

Accordingly, it is preferred that the 1 and 3 volume percent methyltrichlorosilane/pentane solutions penetrate and waterproof the wood to at least 0.75 inches and to at least about 1.5 inches, respectively, with a steady one-pass application. It may be possible to have to spray and treat only one side of a wooden structure (e.g., a fence), because the wood is generally in the dimension of a 1 inch×6 inch board.

EXAMPLE X

A 5 volume percent solution of methyltrichlorosilane/pentane was prepared and introduced to a hand-held garden mister. A 10 volume percent solution of methyltrichlorosilane/pentane was also prepared and introduced to a separate hand-held garden mister. Samples of newsprint, paper-coated polyurethane-filled insulation, and paper used to coat the polyurethane-filled insulation were covered with a fine mist of the 5 volume percent solution. Separate samples of newsprint, paper-coated polyurethane-filled insulation, and paper used to coat the polyurethane-filled insulation were covered with a fine mist of the 10 volume percent solution. Each of the samples were allowed to dry for 20 minutes. Then, droplets of water were placed on each sample. The entire surface was not hydrophobic for any of the samples. Not enough of the preservative composition could be placed on the surfaces of the samples of newsprint or paper to make them hydrophobic. Similarly, the texture of the paper covering the insulation was pocketed and wetted immediately when water was applied to the surface.

In order to determine a more effective way of applying the preservative composition of the present invention, another illustrative preservative composition, in accordance with the present invention, was prepared as detailed in Example XI, below:

EXAMPLE XI

A 5 volume percent solution of methyltrichlorosilane/pentane was prepared and introduced to a hand-pump sprayer. A 10 volume percent solution of methyltrichlorosilane/pentane was also prepared and introduced to a separate hand-pump sprayer. The total volume of each solution was approximately 1 gallon.

In order to determine the effectiveness of the preservative composition prepared in Example XI in treating newsprint, an experiment was carried out as described in Example XII below:

EXAMPLE XII

The 5 volume percent solution of methyltrichlorosilane/pentane prepared in Example XI was sprayed topically on a sample of newsprint. The 10 volume percent solution of methyltrichlorosilane/pentane prepared in Example XI was sprayed topically on a separate sample of newsprint. The samples were allowed to dry for 20 minutes. Water was then placed on each sample. Each of the two treated samples of newsprint was extremely hydrophobic and the water immediately beaded up. Water was also placed on a control sample of untreated newsprint, and the control sample immediately wetted as a result.

Both samples of newsprint turned yellow initially when sprayed. This was not unexpected, due to the presence of lignin in paper. (When exposed to a strong acid, like the HCl formed from the reaction of the silane with the paper, the lignin in the paper will turn yellow. If sufficient primary, secondary, and tertiary amines are present in the paper, the paper will remain yellow.) Here, the yellowness faded over time as the samples of newsprint dried, indicating that little or no amines were present on the surface of the respective samples.

Also, the treated samples of newsprint appeared white, indicating an excess of methyltrichlorosilane was present on each. Thus, a more dilute solution could probably be used, such as a 2 to 3 volume percent solution of methyltrichlorosilane/pentane.

In order to determine the effectiveness of the preservative composition prepared in Example XI in treating paper-coated polyurethane-filled insulation, an experiment was carried out as described in Example XIII below:

EXAMPLE XIII

The 5 volume percent solution of methyltrichlorosilane/pentane prepared in Example XI was sprayed topically on a sample of paper-coated polyurethane-filled insulation. The 10 volume percent solution of methyltrichlorosilane/pentane prepared in Example XI was sprayed topically on a separate sample of paper-coated polyurethane-filled insulation. A third sample of paper-coated polyurethane-filled insulation was treated with neat methyltrichlorosilane. Each sample was allowed to dry for 20 minutes. Water was then placed on each sample. Each of the three treated samples of insulation exhibited strong hydrophobic character. Water was also placed on a control sample of untreated paper-coated polyurethane-filled insulation, and the control sample immediately wetted as a result.

It was observed that neither the methyltrichlorosilane nor the pentane degraded the polyurethane foam of the samples. Moreover, the treated surfaces of the samples of insulation appeared white, indicating an excess of methyltrichlorosilane was present. Thus, a more dilute solution could probably be used, such as a 2 to 3 volume percent solution of methyltrichlorosilane/pentane.

It was determined that neither of the 5 volume percent nor the 10 volume percent of the methyltrichlorosilane/pentane permeated through the insulation samples. Thus, both sides of the sample of the insulation should be treated to prevent water damage. Furthermore, it was observed that it may not be possible to treat a required minimum of 140 board feet of the paper-coated insulation using only 1 gallon of the preservative solution because its surface area is higher compared to that of wood products.

In order to determine the effectiveness of the preservative composition prepared in Example XI in treating the paper that coats the paper-coated polyurethane-filled insulation treated in Example XIII, an experiment was carried out as described in Example XIV below:

EXAMPLE XIV

The 5 volume percent solution of methyltrichlorosilane/pentane prepared in Example XI was sprayed topically on a sample of the paper used to coat the paper-coated polyurethane-filled insulation treated in Example XIII. The 10 volume percent solution of methyltrichlorosilane/pentane prepared in Example XI was sprayed topically on a separate sample of the paper that coats the paper-coated polyurethane-filled insulation treated in Example XIII. Each sample was allowed to dry for 20 minutes. Water was then placed on each sample. The treated surfaces of each of the samples exhibited strong hydrophobic character. Water was also placed on a control sample of untreated paper that coats the paper-coated polyurethane-filled insulation treated in Example XIII, and the control sample immediately wetted as a result.

It was observed that the samples of paper appeared white, indicating an excess of methyltrichlorosilane was present. Thus, a more dilute solution could probably be used, such as a 2 to 3 volume percent solution of methyltrichlorosilane/pentane.

In order to determine the effectiveness of the preservative composition prepared in Example XI in treating drywall, an experiment was carried out as described in Example XV below:

EXAMPLE XV

The 5 volume percent solution of methyltrichlorosilane/pentane prepared in Example XI was sprayed topically on a sample of drywall. The 10 volume percent solution of methyltrichlorosilane/pentane prepared in Example XI was sprayed topically on a separate sample of drywall. Each sample was allowed to dry for 20 minutes. Water was then placed on each sample. The treated surfaces of each of the samples exhibited strong hydrophobic character. Water was also placed on a control sample of untreated drywall, and the control sample immediately wetted as a result.

The treated surfaces of the drywall samples appeared white, indicating an excess of methyltrichlorosilane was present. Thus, a more dilute solution could probably be used, such as a 2 to 3 volume percent solution of methyltrichlorosilane/pentane. Also, it was determined that neither of the 5 volume percent nor the 10 volume percent of the methyltrichlorosilane/pentane permeated through the drywall samples. Thus, both sides of the sample of drywall should be treated to prevent water damage.

In order to determine the effectiveness of the preservative composition prepared in Example XI in treating masonry brick, an experiment was carried out as described in Example XVI below:

EXAMPLE XVI

The 10 volume percent solution of methyltrichlorosilane/pentane prepared in Example XI was sprayed topically on a sample of masonry brick. The sample was allowed to dry for 20 minutes. Water was then placed on the sample. Water immediately beaded up when placed on the sample surface. Water was also placed on a control sample of untreated masonry brick, and the control sample immediately wetted as a result.

The treated surfaces of the masonry brick samples appeared white, indicating an excess of methyltrichlorosilane was present. Thus, a more dilute solution could probably be used, such as a 2 to 3 volume percent solution of methyltrichlorosilane/pentane. Also, the treated sample of masonry brick was treated only on one surface, and the methyltrichlorosilane/pentane did not appear to permeate the entire surface. The untreated portion of the sample wetted immediately with the presence of water. Thus, in order to make masonry brick completely hydrophobic, the entire brick would have to be sprayed.

The present invention has been described in an illustrative manner. It is to be understood that the terminology, which has been used, is intended to be in the nature of words of description rather than of limitation.

Many modifications and variations of the present invention are possible in light of the above teachings. Therefore, the present invention may be practiced other than as specifically described.

What is claimed is:

1. A method for preserving a material comprising:
   providing a preservative composition comprising at least one silane-containing material and at least one hydrocarbon alkane solvent containing molecules of at least five carbon atoms;
   applying the preservative composition to the material and penetrating and diffusing the silane-containing material into the material; and
   wherein the at least one silane-containing material is methyltrichlorosilane.

2. A method as set forth in claim 1 wherein the preservative composition further comprises at least one pesticide-containing material.

3. A method for preserving a material comprising:
   providing a preservative composition comprising at least one silane-containing material and at least one hydrocarbon alkane solvent containing molecules of at least five carbon atoms;
   applying the preservative composition to the material and penetrating and diffusing the silane-containing material into the material;
   wherein the preservative composition further comprises at least one pesticide-containing material; and
   wherein the at least one pesticide-containing material is boric anhydride.

4. A method for preserving an insulation material comprising:
   providing a preservative composition comprising at least one silane-containing material and at least one hydrocarbon solvent containing molecules of at least five carbon atoms; and
   applying the preservative composition to the insulation material.

5. A method as set forth in claim 4 wherein the at least one hydrocarbon solvent is at least one of pentane, heptane, hexane, and combinations thereof.

6. A method as set forth in claim 4 wherein the at least one silane-containing material is methyltrichlorosilane.

7. A method as set forth in claim 4 wherein the preservative composition further comprises at least one pesticide-containing material.

8. A method as set forth in claim 7 wherein the at least one pesticide-containing material is boric anhydride.

9. A method for preserving a drywall material comprising:
   providing a preservative composition comprising at least one silane-containing material and at least one hydrocarbon alkane solvent containing molecules of at least five carbon atoms; and
   applying the preservative composition to the drywall material and penetrating and diffusing the silane-containing material into the drywall material.

10. A method as set forth in claim 9 wherein the at least one hydrocarbon alkane solvent is at least one of pentane, heptane, hexane, and combinations thereof.

11. A method for preserving a drywall material comprising:
    providing a preservative composition comprising at least one silane-containing material and at least one hydrocarbon solvent containing molecules of at least five carbon atoms; and
    applying the preservative composition to the drywall material; and wherein the at least one silane-containing material is methyltrichlorosilane.

12. A method for preserving a drywall material comprising:
   providing a preservative composition comprising at least one silane-containing material and at least one hydrocarbon solvent containing molecules of at least five carbon atoms; and
   applying the preservative composition to the drywall material; and
   wherein the preservative composition further comprises at least one pesticide-containing material.

13. A method as set forth in claim 12 wherein the at least one pesticide-containing material is boric anhydride.

14. A method for preserving a masonry material comprising:
   providing a preservative composition comprising at least one silane-containing material and at least one hydrocarbon solvent containing molecules of at least five carbon atoms; and
   applying the preservative composition to the masonry material; and
   wherein the at least one silane-containing material is methyltrichlorosilane.

15. A method for preserving a masonry material comprising:
   providing a preservative composition comprising at least one silane-containing material and at least one hydrocarbon solvent containing molecules of at least five carbon atoms; and
   applying the preservative composition to the masonry material; and
   wherein the preservative composition further comprises at least one pesticide-containing material.

16. A method as set forth in claim 15 wherein the at least one pesticide-containing material is boric anhydride.

17. A method for preserving a wood material comprising:
   providing a preservative composition comprising at least one silane-containing material and at least one hydrocarbon solvent containing molecules of at least five carbon atoms;
   applying the preservative composition to the wood material; and
   wherein the at least one silane-containing material is methyltrichlorosilane.

18. A method as set forth in claim 17 wherein the preservative composition further comprises at least one pesticide-containing material.

19. A method as set forth in claim 18 wherein the at least one pesticide-containing material is boric anhydride.

20. A preservative composition comprising:
   at least one silane-containing material;
   at least one hydrocarbon alkane solvent containing molecules of at least five carbon atoms to allow the silane-containing material to penetrate and diffuse into a material contacted by the preservative composition; and
   wherein said at least one silane-containing material is methyltrichlorosilane.

21. A preservative composition comprising:
   at least one silane-containing material;
   at least one hydrocarbon alkane solvent containing molecules of at least five carbon atoms to allow the silane-containing material to penetrate and diffuse into a material contacted by the preservative composition; and
   at least one pesticide-containing material.

22. A preservative composition as set forth in claim 21 wherein said at least one pesticide-containing material is boric anhydride.

* * * * *

UNITED STATES PATENT AND TRADEMARK OFFICE
CERTIFICATE OF CORRECTION

PATENT NO. : 7,192,470 B2 Page 1 of 1
APPLICATION NO. : 11/039515
DATED : March 20, 2007
INVENTOR(S) : Edwin Neal and Michael M. Thompson It is certified that error appears in the above-identified patent and that said Letters Patent is hereby corrected as shown below:

Column 3, line 20, "lodotrimethylsilane" should read -- Iodotrimethylsilane --.

Column 3, line 36, after "least" insert -- one --;

Column 4, line 19, after "fuel", delete "may be used"; and

Column 4, line 27, "1.0 µm", should read -- 1.0 gm --.

Signed and Sealed this

Twentieth Day of May, 2008

JON W. DUDAS
*Director of the United States Patent and Trademark Office*